(12) United States Patent
Tanimoto et al.

(10) Patent No.: US 6,545,178 B1
(45) Date of Patent: Apr. 8, 2003

(54) METHOD FOR PRODUCTION OF ACROLEIN AND ACRYLIC ACID FROM PROPYLENE

(75) Inventors: Michio Tanimoto, Hyogo-ken (JP); Daisuke Nakamura, Hyogo-ken (JP); Tatsuya Kawajiri, Kanagawa-ken (JP)

(73) Assignee: Nippon Shokubai Co., Ltd., Osaka (JP)

( * ) Notice: Subject to any disclaimer, the term of this patent is extended or adjusted under 35 U.S.C. 154(b) by 0 days.

(21) Appl. No.: 09/314,719

(22) Filed: May 18, 1999

(30) Foreign Application Priority Data

May 18, 1998 (JP) ............................. 10-135417

(51) Int. Cl.$^7$ .................... C07C 51/16; C07C 45/35
(52) U.S. Cl. ................ 562/547; 562/535; 562/549; 568/477; 568/478; 568/479
(58) Field of Search ................ 562/535, 547, 562/549; 568/477, 478, 479

(56) References Cited

U.S. PATENT DOCUMENTS

| | | | |
|---|---|---|---|
| 1,147,885 A | * 7/1915 | Peabody et al. | |
| 3,799,978 A | 3/1974 | Ohara et al. | ............ 260/533 N |
| 3,876,693 A | 4/1975 | Erpenbach et al. | ..... 260/530 N |
| 4,147,885 A | 4/1979 | Shimizu et al. | ............. 562/535 |
| 5,684,188 A | * 11/1997 | Hefner et al. | |
| 5,705,684 A | * 1/1998 | Hefner et al. | |
| 5,739,392 A | 4/1998 | Tanimoto et al. | ........... 562/535 |

FOREIGN PATENT DOCUMENTS

| | | | |
|---|---|---|---|
| EP | 0 194 620 A | 9/1986 | ........... C07C/57/04 |
| EP | 0 731 077 | * 11/1996 | |
| GB | 1 289 057 A | 9/1972 | |

* cited by examiner

*Primary Examiner*—Porfirio Nazario-Gonzalez
(74) *Attorney, Agent, or Firm*—Fish & Richardson P.C.

(57) ABSTRACT

In the production of acrolein and acrylic acid by the catalytic gas phase oxidation of propylene with a molecular oxygen-containing gas, a method is provided which enables acrolein and acrylic acid to be stably produced with a high yield for a long time from propylene by effectively repressing such secondary reactions as are responsible for the formation of organic acids, high boiling compounds, and tarry compounds, the deposition of carbonized materials, and the deterioration of the quality of products. The content of unsaturated hydrocarbons (excluding propylene) of 2–5 carbon atoms in the raw material for propylene is kept below 500 ppm (by weight). Particularly, it is proper to use a raw material for propylene which has a content of unsaturated hydrocarbons (excluding propylene) of 2–5 carbon atoms of not more than 200 ppm (by weight) and a total content of diene and acetylenic compounds of 2–5 carbon atoms of not more than 200 ppm (by weight). The reaction scheme is shown below:

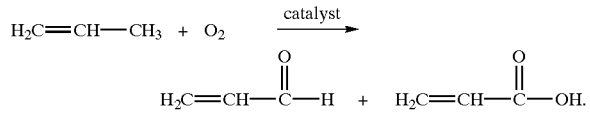

12 Claims, No Drawings

METHOD FOR PRODUCTION OF ACROLEIN AND ACRYLIC ACID FROM PROPYLENE

BACKGROUND OF THE INVENTION

1. Field of the Invention

This invention relates to a method for the production of acrolein and acrylic acid. More particularly, in the production of acrolein and acrylic acid by the catalytic gas phase oxidation of propylene with a molecular oxygen-containing gas, the present invention relates to a method for enabling acrolein and acrylic acid to be stably produced with a high yield for a long time while effectively repressing the formation of such by-products as various aldehydes, carboxylic acids, high boiling compounds, and tarry substances without impairing the performance of a catalyst.

2. Description of the Related Art

The practice of producing acrolein and acrylic acid by the catalytic gas phase oxidation of propylene with a molecular oxygen-containing gas is widely prevailing on a commercial scale. Generally, the production of acrylic acid is effected by a two-step reaction which comprises a former step of producing acrolein mainly by the gas phase oxidation of propylene with a molecular oxygen-containing gas and a latter step of further oxidizing the reaction gas containing the acrolein thereby producing acrylic acid.

At the former step for oxidizing propylene with a molecular oxygen-containing gas, however, a side reaction occurs to produce organic acids such as terephthalic acid and maleic acid, high boiling compounds, and tarry compounds besides the main reaction which produces acrolein. As a result, these by-products contaminate the reaction apparatus and, in an extreme case, prevent the reaction apparatus from being normally operated because they form deposits such as carbonized materials, aggravate pressure drop, and plug pipes or degrades the quality of product. If the reaction apparatus is provided with purification means for the removal of these by-products, the provision will entail such problems as increasing the cost of equipment, boosting the cost of production. Further, acrolein and other highly reactive compounds give rise to after reaction.

Heretofore, for the purpose of repressing these side reactions, such measures as suddenly cooling the outlet gas of a reaction vessel of the former step thereby repressing the formation of side reactions or retaining the temperature of the outlet gas of the reactor above a fixed level thereby repressing the contamination of a reaction apparatus due to the deposition of high boiling compounds and tarry compounds have been resorted to (as disclosed in U.S. Pat. No. 3,876,693, for example).

These measures, however, necessitate special devices adapted exclusively for their own purposes and entail consumption of a large amount of energy for cooling or heating and consequently prove economically disadvantageous because of an inevitable addition to the cost of production. Besides, they are deficient in effect. Especially, they are not ratable as fully effective regarding the contamination of the apparatus with organic acids, high boiling compounds, and tarry compounds, the deposition of carbonized materials, and the deterioration of the quality of product.

As concerns the reclamation of a reaction product gas as part of a material gas, a method for limiting the amount of organic compounds such as organic acids has been proposed (as disclosed in U.S. Pat. No. 4,147,885, for example). This patent application, however, has absolutely no mention of the quality of the raw material propylene gas.

It is an object of this invention, therefore, to provide in the production of acrolein and acrylic acid by the catalytic gas phase oxidation of propylene with a molecular oxygen-containing gas, a method which enables acrolein and acrylic acid to be stably produced with a high yield for a long time from propylene by effectively repressing such side reactions as are responsible for the formation of organic acids, high boiling compounds, and tarry compounds, the deposition of carbonized materials, and the deterioration of the quality of products.

This invention, in a process of two-step reaction for the production of acrylic acid by the catalytic gas phase oxidation of propylene with a molecular oxygen-containing gas, is directed at providing a method for stably and continuously for a long time producing acrolein mainly from propylene with a high yield and consequently producing acrylic acid ultimately with a high yield by effectively repressing such side reactions as are responsible for the formation of organic acids, high boiling compounds, and tarry compounds, the deposition of carbonized materials, and the deterioration of the quality of products.

SUMMARY OF THE INVENTION

We have performed a study with a view to solving the problems encountered in the production of acrolein and acrylic acid by the catalytic gas phase oxidation of propylene with a molecular oxygen-containing gas as described above and, as a result, have acquired the following knowledge.

(1) The organic acids, high boiling compounds, and tarry compounds are formed by the side reactions irrespectively of differences in reaction conditions, activity of catalyst, or selectivity of the formation of acrolein.

(2) While these by-products occur only in extremely small amounts as compared with acrolein and acrylic acid which are main products, they form a serious hindrance to a continuous and stable operation.

(3) The amounts of their formation are affected more by the impurities contained in the raw material propylene and their amounts than by the performance of a catalyst.

(4) The presence of unsaturated compounds other than propylene largely affects the performance of a catalyst and the amounts of by-products to be formed.

(5) The effects on the performance of a catalyst and the amounts of by-products to be formed increase in accordance as the degree of unsaturation of impurities in propylene is heightened or the basicity gains in intensity.

Then, we have continued the study and have discovered that the side reactions are effectively repressed and the problems mentioned above are consequently solved by lowering the total content of unsaturated hydrocarbons of 2–5 carbon atoms other than propylene in the raw material propylene below 500 ppm (by weight). The present invention has been perfected based on this knowledge.

Specifically, in the production of acrolein and acrylic acid by the catalytic gas phase oxidation of propylene with a molecular oxygen-containing gas in the presence of an oxidation catalyst, this invention concerns a method for the production of acrolein and acrylic acid which comprises lowering the total content of unsaturated hydrocarbons of 2–5 carbon atoms (excluding propylene) in the raw material propylene below 500 ppm (by weight).

Further in the production of acrylic acid by a two-step reaction comprising a former step for producing acrolein mainly by the catalytic gas phase oxidation of propylene with a molecular oxygen-containing gas in the presence of an oxidation catalyst and a latter step for producing acrylic acid by the gas phase oxidation of the acrolein-containing reaction gas in the presence of an oxidation catalyst, this invention concerns a method for the production of acrylic acid which comprises lowering the total content of unsaturated hydrocarbons of 2–5 carbon atoms (excluding propylene) in the raw material propylene below 500 ppm (by weight).

DESCRIPTION OF THE PREFERRED EMBODIMENT

The characteristic feature of this invention comprises using a raw material propylene of which the total content of unsaturated hydrocarbons of 2–5 carbon atoms except that propylene (hereinafter referred to simply as "unsaturated hydrocarbons of 2–5 carbon atoms") is below 500 ppm (ppm by weight; applicable similarly hereinafter). The content of the unsaturated hydrocarbons of 2–5 carbon atoms is preferred to be not more than 450 ppm, more preferred to be not more than 300 ppm, and particularly preferred to be not more than 200 ppm.

In this invention, propylene having a content of unsaturated hydrocarbons of 2–5 carbon atoms of not more than 500 ppm, preferably not more than 450 ppm, more preferably not more than 300 ppm, and particularly preferably not more than 200 ppm and also having a total content of diene and acetylenic compounds of 2–5 carbon atoms of not more than 200 ppm, preferably not more than 150 ppm, more preferably not more than 100 ppm, and particularly preferably not more than 50 ppm is used advantageously. As one ideal example of the raw material propylene, propylene having a content of unsaturated hydrocarbons of 2–5 carbon atoms of not more than 200 ppm and a total content of diene and acetylenic compounds of 2–5 carbon atoms of not more than 100 ppm, particularly preferably not more than 50 ppm may be cited.

Butadiene may be cited as a typical example of the diene and methyl acetylene as a typical example of the acetylenic compounds, both mentioned above. As other typical examples of the unsaturated hydrocarbons of 2–5 carbon atoms, ethylene, butylene, and isobutylene may be cited.

It is such saturated hydrocarbons as propane that account for the largest proportion of the impurities in the raw material propylene. No particular limit is imposed on the content of such saturated hydrocarbons because these saturated hydrocarbons have low reactivity with a catalyst and exert only small influence on the performance and service life of the catalyst. In contrast, unsaturated hydrocarbons have high reactivity with a catalyst, induce side reactions, and by-produced substances other than the compounds aimed at. In addition to lowering the catalytic activity and decreasing the yields of acrolein and acrylic acid, the unsaturated hydrocarbons form a cause for impairing the service life of the catalyst. Further, the by-products form one cause for the generation of after reactions, contaminate a reaction apparatus, and cause plugging of pipes. Thus, the concentration of unsaturated hydrocarbons in the raw material propylene must be strictly controlled.

The raw material propylene contains involatile residues and sulfur components in addition to the saturated and unsaturated hydrocarbons mentioned above. These impurities form a cause for degradation of the capacity of a propylene evaporator and a cause for corrosion of the reaction apparatus. It is, therefore, proper to keep the contents of involatile residues and sulfur components each below 100 ppm (by weight), preferably below 50 ppm (by weight).

The raw material propylene usable herein does not impose any restriction particularly but only requires to have the content of unsaturated hydrocarbons within the range mentioned above. For example, the species of propylene produced by the method of steam cracking of naphtha and the species of propylene produced by the method of dehydrogenation or oxidative dehydrogenation of propane can be used as the raw material propylene. The method for adjusting the content of unsaturated hydrocarbons in such propylene does not impose any restriction particularly. In the case of the method of steam cracking naphtha, for example, this adjustment may be accomplished by separating the unsaturated hydrocarbons by the technique of low-temperature fractional distillation and then removing acetylenic compounds entrained by the unsaturated hydrocarbons in a minute amount by selective hydrogenation. The propylene may be otherwise purified by super precision distillation using an increased number of steps.

No particular limit is imposed on the purity of propylene in the raw material propylene. In consideration of the economy to be associated with the purification, the raw material propylene having a purity of propylene of not less than 90%, preferably not less than 92%, is advantageously used.

Incidentally, the content of unsaturated hydrocarbons of 2–5 carbon atoms in the raw material propylene is preferred to be as small as possible. If this content is lowered to below 1 ppm, however, a further improvement in yield enough to offset the increase in cost due to the extra work of purification will not be recognized. It is enough for the contents of diene and acetylenic compounds of 2–5 carbon atoms to be lowered to the neighborhood of 0.1 ppm.

The production of acrolein and acrylic acid from propylene and the production of acrylic acid by a two-step reaction from propylene which are contemplated by this invention can be carried out by a method which is generally used or which is known to be used except that the point that the raw material propylene to be used ought to have a content of unsaturated hydrocarbons of 2–5 carbon atoms of not more than 500 ppm.

As respects the catalyst for the production, for example, a catalyst which is generally used for the production of acrolein and acrylic acid from propylene and the production of acrylic acid by a two-step reaction from propylene can be used. In the production of acrylic acid by the two-step reaction, for example, a metal oxide catalyst having molybdenum and bismuth as essential components may be used as the oxidation catalyst in the former step. Among other metal oxide catalysts conceivable herein, oxidation catalysts represented by the general formula (1) may be cited as preferable examples.

$$Mo_aBi_bFe_cA_dB_eC_fD_gO_x \tag{1}$$

In the formula, Mo is molybdenum, Bi is bismuth, Fe is iron, A is at least one element selected from the group consisting of cobalt and nickel, B is at least one element selected from the group consisting of alkali metals, alkaline earth metals, and thallium, C is at least one element selected from the group consisting of tungsten, silicon, aluminum, zirconium, and titanium, D is at least one element selected from the group consisting of phosphorus, tellurium, antimony, tin, cerium, lead, niobium, manganese, arsenic, and zinc, O is oxygen, and a, b, c, d, e, f, g, and x is the atomic ratios respectively of Mo, Bi, Fe, A, B, C, D, and O such that b=0.1–10, c=0.1–20, d=2–20, e=0.001–10, f=0–30, g=0–4, and x is a numerical value to be determined by the state of oxidation of the component elements.

The oxidation catalyst may be in the shape of cylinders, rings, or spheres or may be in an amorphous form. Optionally, it may be supported on an inert carrier or it may be obtained by molding an active component by a suitable method. Besides the components mentioned above, the oxidation catalyst may incorporate additionally therein a molding additives and a reinforcing agent. For example, various glass fibers and whiskers may be used for the incorporation.

The oxidation catalyst does not need to be limited to a simple species. It is allowed to have part thereof diluted with an inert carrier. Alternatively, several species of oxidation catalysts of varying activity prepared by altering components, method of manufacture, and conditions of calcination may be used in a combined form.

As the reactor, a shell-and-tube type fixed bed reactor is generally adopted. It is also allowable to use a fluidized bed type reactor or a moving bed type reactor. The reactor is not particularly discriminated on account of the kind of material used therefor. It may be made of carbon steel or stainless steel, for example.

The molecular oxygen-containing gas source is not limited to pure oxygen. Air and waste gases emanating from various plants may be suitably used. Other impurities than the unsaturated hydrocarbons mentioned above, namely carbon dioxide gas and other impurities such as NOx, SOx, and moisture which occur in such amounts as found in the standard air bring no particular effect.

The unreacted propylene which remains after such soluble components as acrylic acid have been recovered and separated by the use of a solvent formed substantially of water or other solvent from the acrylic acid-containing reaction gas obtained at the latter step in the production of acrylic acid by the catalytic gas phase oxidation such as, for example, a two-step reaction, of propylene can be circulated and used wholly or partly as the raw material gas. In this case, the raw material propylene which is composed of the propylene so circulated and the propylene to be freshly supplied is only required to have a content of unsaturated hydrocarbons of 2–5 carbon atoms of not more than 500 ppm, preferably not more than 450 ppm, more preferably not more than 300 ppm, and particularly preferably not more than 200 ppm and a total content of diene and acetylenic compounds of 2–5 carbon atoms of not more than 200 ppm, preferably not more than 150 ppm, more preferably not more than 200 ppm, and particularly preferably not more than 50 ppm.

The method of this invention is executed by first packing a shell-and-tube type reactor with the oxidation catalyst mentioned above and passing a raw material gas composed of raw material propylene, a molecular oxygen-containing gas, and an optionally incorporated inert gas through the reaction zone of the reactor at a reaction temperature in the range of 250–450° C., preferably in the range of 280°–400° C., at a space velocity in the range of 300–5,000 $hr^{-1}$, preferably in the range of 700–3,000 $hr_{-1}$.

Since this invention effectively represses side reactions, it can solve such problems as by-products of organic acids, high boiling compounds, and tarry compounds, deposition of carbonized materials, consequent aggravation of pressure drop, plugging of tubes, and deterioration of quality of product.

According to this invention, the deterioration of the performance of the oxidation catalyst to be used can be repressed effectively. By this invention, therefore, acrolein and acrylic acid can be stably produced continuously for a long time with a high yield from propylene. Particularly in the case of producing acrylic acid by the two-step reaction, acrolein is mainly produced from propylene with a high yield at the former step and consequently acrylic acid is produced with a high yield at the latter step, stably for a long time.

Now, this invention will be described more specifically below with reference to working examples. The degree of conversion of propylene, the yield of acrolein, and the yield of acrylic acid have been determined in accordance with the following formulas.

Conversion of propylene (%)=[(Amount of propylene spent in the reaction)/(Amount of propylene supplied)]×100

Yield of acrolein (%)=[(Amount of acrolein formed)/(Amount of propylene supplied)]×100

Yield of acrylic acid (%)=[(Amount of acrylic acid formed)/(Amount of propylene supplied)]×100

The content of unsaturated hydrocarbons of 2–5 carbon atoms and the total content of diene and acetylenic compounds have been determined by the analysis of gas chromatography.

EXAMPLE 1

Preparation of Catalyst

A catalyst was prepared as follows in accordance with the method described in Example 1 of U.S. Pat. No. 3,799,978. In 1500 ml of water which was kept heated and stirred, 1062 g of ammonium molybdate and 314 g of ammonium paratungstate were dissolved. To the resultant aqueous solution, a mixed aqueous nitrate solution consisting of an aqueous solution having 700 g of cobalt nitrate dissolved in 200 ml of distilled water, an aqueous solution having 243 g of ferric nitrate dissolved in 200 ml of distilled water, and an aqueous solution having 292 g of bismuth nitrate dissolved in 300 ml of distilled water acidified in advance by addition of 60 ml of concentrated nitric acid was added dropwise. Subsequently, an aqueous solution having 244 g of 20% by weight silica sol solution and 2.02 g of potassium hydroxide dissolved in 150 ml of distilled water was added thereto. The suspension thus formed was heated and stirred, evaporated, and then molded in a cylindrical shape 5 mm in diameter, and calcined in a stream of air at the highest temperature of 450° C. for 6 hours to obtain a catalyst. The composition (excluding oxygen) of metal elements of this catalyst by atomic ratio was as follows.

$Mo_{12}Bi_{1.2}Fe_{1.2}Co_{4.5}W_{2.4}K_{0.07}Si_{1.62}$ (Oxidation Reaction)

A reaction tube of stainless steel, 25 mm in inside diameter and 4,200 mm in length, immersed in a fused-salt bath kept at a substantially uniform temperature was packed with the catalyst mentioned above so as to form a catalyst bed 3,000 mm in length. A reaction gas composed of propylene of a concentration of 6.5% by volume, 65% by volume of air, and the balance of steam was supplied to the reaction tube at a space velocity of 1800 $hr^{-1}$ and allowed to react at a temperature of 325° C. The propylene mentioned above had the following composition.

Propylene: 96% by volume

Propane and other components: Balance

Content of unsaturated hydrocarbons of 2–5 carbon atoms: 47 ppm

Content of diene and acetylenic compounds: 10 ppm

The results of the initial stage of reaction and those of the reaction continued for 4,000 hours were as shown below.

(Initial Stage of Reaction)

Conversion of propylene: 96.5 mol %

Yield of acrolein: 78.5 mol %

Yield of acrylic acid: 10 mol %

(After 4000 Hours)

Conversion of propylene: 96.0 mol %

Yield of acrolein: 79.0 mol %

Yield of acrylic acid: 9.7 mol %

EXAMPLE 2

A catalyst having the following composition (excluding oxygen) was prepared by following the procedure for the preparation of catalyst of Example 1.

$$Mo_{12}Bi_{1.2}Fe_{1.2}Co_{5.8}K_{0.05}Ce_{1.2}Nb_{0.5}Si_{1.62}$$

Subsequently, propylene was oxidized by following the procedure of Example 1. The propylene used herein had the following composition.

Propylene: 96% by volume

Propane and other components: Balance

Content of unsaturated hydrocarbons of 2–5 carbon atoms: 450 ppm

Content of diene and acetylenic compounds: 70 ppm

The results of the initial stage of reaction and those of the reaction continued for 4, 000 hours were as shown below.

(Initial Stage of Reaction)

Conversion of propylene: 96.0 mol %

Yield of acrolein: 77.8 mol %

Yield of acrylic acid: 10.5 mol %

(After 4,000 Hours)

Conversion of propylene: 95.6 mol %

Yield of acrolein: 78.2 mol %

Yield of acrylic acid: 9.8 mol %

Control 1

A reaction was carried out by following the procedure of Example 1 while using propylene of the following composition instead as the propylene.

Propylene: 91% by volume

Propane and other components: Balance

Content of unsaturated hydrocarbons of 2–5 carbon atoms: 800 ppm

Content of diene and acetylenic compounds: 50 ppm

The results of the initial stage of reaction and those of the reaction continued for 4,000 hours were as shown below.

(Initial Stage of Reaction)

Conversion of propylene: 95.5 mol %

Yield of acrolein: 77.2 mol %

Yield of acrylic acid: 9.5 mol %

(After 4,000 Hours)

Conversion of propylene: 94.5 mol %

Yield of acrolein: 76.2 mol %

Yield of acrylic acid: 8.8 mol %

Control 2

A reaction was carried out by following the procedure of Example 2 while using propylene of the following composition instead as the propylene.

Propylene: 96% by volume

Propane and other components: Balance

Content of unsaturated hydrocarbons of 2–5 carbon atoms: 600 ppm

Content of diene and acetylenic compounds: 250 ppm

The results of the initial stage of reaction and those of the reaction continued for 4,000 hours were as shown below.

(Initial Stage of Reaction)

Conversion of propylene: 95.8 mol %

Yield of acrolein: 75.5 mol %

Yield of acrylic acid: 8.7 mol %

(After 4,000 Hours)

Conversion of propylene: 94.5 mol %

Yield of acrolein: 74.2 mol %

Yield of acrylic acid: 7.9 mol %

EXAMPLE 3

A shell-and-tube type reaction apparatus (1) fitted with an accessory device for cooling a reaction formed gas and a shell-and-tube type reaction apparatus (2) independent thereof were connected with a piping. The reaction apparatus (1) was packed with the same catalyst as used in Example 1 so as to form a catalyst bed, 3,000 mm in length, and the reaction apparatus (2) was packed with a catalyst of the following composition (prepared by the method described in Example 1 of U.S. Pat. No. 5,739,392):

$$Mo_{12}V_{5.5}W_1Cu_{2.7}$$

so as to form a catalyst bed, 3000 mm in length. The reaction formed gas obtained in the reaction apparatus (1) was cooled immediately to below 280° C. at the outlet of the catalyst bed so as to preclude the occurrence of after reactions. The piping connecting the reaction apparatus (1) and the reaction apparatus (2) was kept heated to 260° C. The residence time of the gas in the piping was set below 5 seconds.

As the propylene, the propylene of the following composition was used.

Propylene: 96% by volume

Propane and other components: Balance

Content of unsaturated hydrocarbons of 2–5 carbon atoms: 47 ppm

Content of diene and acetylenic compounds: 10 ppm

The reaction was carried out by fixing the reaction temperature of the reaction apparatus (1) at 325° C. and the reaction temperature of the reaction apparatus (2) at 265° C., and by feeding a reaction gas comprising 6% by volume of propylene, 60% by volume of air and a balance of steam at 1,500 hr$^{-1}$ of space velocity. The combined performance of catalyst in the reaction apparatus (1) and the reaction apparatus (2) during the initial stage of reaction was as follows.

(Initial Stage of Reaction)

Conversion of propylene: 96.7 mol %

Yield of acrylic acid: 89.2 mol %

Yield of acrolein: 0.5 mol %

After the reaction was continued for 4,000 hours, the reaction apparatus (1) and the reaction apparatus (2) were equal in temperature and the combined performance of these reaction apparatuses was as shown below.

(After 4,000 Hours)

Conversion of propylene: 96.1 mol %

Yield of acrylic acid: 88.7 mol %

Yield of acrolein: 0.7 mol %

During the course of the reaction mentioned above, no discernible change was recognized in the pressure drop after the catalyst bed of the reaction apparatus (1).

Control 3

A reaction was carried out by following the procedure of Example 3 while using the propylene of the following composition as the propylene.

Propylene: 88% by volume

Propane and other components: Balance

Content of unsaturated hydrocarbons of 2–5 carbon atoms: 1600 ppm

Content of diene and acetylenic compounds: 250 ppm

The combined performance of catalyst in the reaction apparatus (1) and the reaction apparatus (2) during the initial stage of reaction was as follows.

(Initial Stage of Reaction)

Conversion of propylene: 94.3 mol %

Yield of acrylic acid: 78.8 mol %

Yield of acrolein: 3.9 mol %

After the reaction was continued for 4,000 hours, the reaction apparatus (1) and the reaction apparatus (2) were equal in temperature and the combined performance of these reaction apparatuses was as shown below.

(After 4,000 Hours)

Conversion of propylene: 92.7 mol %

Yield of acrylic acid: 75.8 mol %

Yield of acrolein: 4.3 mol %

During the course of the reaction mentioned above, the pressure drop after the catalyst bed of the reaction apparatus (1) increased by 400 mm in water column. The reaction was stopped and the reaction apparatuses were examined in search of the cause for the rise of pressure drop. Consequently, the search resulted in detecting formation of carbonized materials from the outlet part of the catalyst bed of the reaction apparatus (1) through the inlet part of the catalyst bed of the reaction apparatus (2). The formation of carbonized materials was found to be responsible for the rise of pressure drop.

What is claimed is:

1. A method for the production of acrolein and acrylic acid which comprises oxidizing raw material propylene containing unsaturated hydrocarbons of 2–5 carbon atoms (excluding propylene) in an amount of below 500 ppm (by weight) with a molecular oxygen-containing gas in gas phase in the presence of an oxidation catalyst.

2. A method according to claim 1, wherein the content of unsaturated hydrocarbons of 2–5 carbon atoms is lowered below 450 ppm (by weight).

3. A method according to claim 1, wherein the total content of diene and acetylenic compounds of 2–5 carbon atoms in the raw material for propylene is not more than 200 ppm (by weight).

4. A method according to claim 1, wherein the content of unsaturated hydrocarbons of 2–5 carbon atoms is lowered below 300 ppm (by weight).

5. A method according to claim 1, wherein the total content of diene and acetylenic compounds of 2–5 carbon atoms in the raw material for propylene is not more than 150 ppm (by weight).

6. A method according to claim 1, wherein the contents of involatile residue and sulfur components in the raw material for propylene were respectively not more than 100 ppm (by weight) and not more than 100 ppm (by weight).

7. A method for the production of acrylic acid which comprises oxidizing raw material propylene containing unsaturated hydrocarbons of 2–5 carbon atoms (excluding propylene) in an amount of below 500 ppm (by weight) in a two-step reaction, wherein the first step is producing an acrolein-containing reaction gas mainly by oxidizing the propylene with a molecular oxygen-containing gas in gas phase in the presence of an oxidization catalyst, and the second step is producing acrylic acid by oxidizing the acrolein-containing reaction gas in gas phase in the presence of an oxidation catalyst.

8. A method according to claim 7, wherein the content of unsaturated hydrocarbons of 2–5 carbon atoms is lowered below 450 ppm (by weight).

9. A method according to claim 7, wherein the total content of diene and acetylenic compounds of 2–5 carbon atoms in the raw material for propylene is not more than 200 ppm (by weight).

10. A method according to claim 7, wherein the content of unsaturated hydrocarbons of 2–5 carbon atoms is lowered below 300 ppm (by weight).

11. A method according to claim 7, wherein the total content of diene and acetylenic compounds of 2–5 carbon atoms in the raw material for propylene is not more than 150 ppm (by weight).

12. A method according to claim 1, wherein the contents of involatile residue and sulfur components in the raw material for propylene were respectively not more than 100 ppm (by weight) and not more than 100 ppm (by weight).

* * * * *